(12) United States Patent
Newcomb

(10) Patent No.: US 7,889,330 B2
(45) Date of Patent: Feb. 15, 2011

(54) METHOD OF TAKING AN IMAGE OF AN OBJECT RESIDING IN A TRANSPARENT, COLORED CONTAINER

(75) Inventor: David Newcomb, Morrisville, NC (US)

(73) Assignee: Parata Systems, LLC, Durham, NC (US)

( * ) Notice: Subject to any disclaimer, the term of this patent is extended or adjusted under 35 U.S.C. 154(b) by 189 days.

(21) Appl. No.: 12/249,402

(22) Filed: Oct. 10, 2008

(65) Prior Publication Data

US 2010/0091285 A1 Apr. 15, 2010

(51) Int. Cl.
G01N 21/65 (2006.01)
G01N 21/90 (2006.01)

(52) U.S. Cl. .................... 356/73; 356/301; 356/239.6

(58) Field of Classification Search .................. 356/427, 356/239.5, 239.6, 73
See application file for complete search history.

(56) References Cited

U.S. PATENT DOCUMENTS

| 6,535,637 | B1 | 3/2003 | Wootton et al. |
| 6,771,369 | B2 | 8/2004 | Rzasa et al. |
| 7,028,723 | B1 | 4/2006 | Alouani et al. |
| 7,218,395 | B2 | 5/2007 | Kaye et al. |
| 2004/0183237 | A1 | 9/2004 | McGrath et al. |
| 2005/0134856 | A1 | 6/2005 | Rutledge |
| 2008/0183410 | A1 | 7/2008 | Klein et al. |
| 2010/0128165 | A1* | 5/2010 | Newcomb et al. ............ 348/370 |

FOREIGN PATENT DOCUMENTS

| CN | 101118363 A | * | 6/2008 |
| EP | 1 003 027 A1 | | 5/2000 |

OTHER PUBLICATIONS

The International Search Report and the Written Opinion for International Application No. PCT/US2009/057383, mailed Dec. 7, 2009.

* cited by examiner

*Primary Examiner*—F. L Evans
(74) *Attorney, Agent, or Firm*—Myers Bigel Sibley & Sajovec

(57) ABSTRACT

A method of producing an image of an object residing inside a transparent container of a first color includes: illuminating the container and the object with light of a second color, the second color being substantially the inverse of the first color; and producing an image of the object through the container. An image produced by this method can exhibit substantially the same color as the object itself, even when the image is taken through a colored transparent wall.

18 Claims, 4 Drawing Sheets
(3 of 4 Drawing Sheet(s) Filed in Color)

METHOD OF TAKING AN IMAGE OF AN OBJECT RESIDING IN A TRANSPARENT, COLORED CONTAINER

FIELD OF THE INVENTION

The present invention is directed generally to imaging, and more particularly to imaging of an object within a container.

BACKGROUND OF THE INVENTION

There is an ongoing and predicted long-term shortage of licensed pharmacists. Due to the increasing age of the population and the ever-increasing number of prescription medicines available, the demand for prescription drugs is growing at rate that will far exceed the capacity and numbers of licensed pharmacists. The net impact of this imbalance is that pharmacists are increasingly spending more time doing clerical and administrative tasks such as verifying filled prescriptions and checking data entry done by pharmacy technicians. Since the capacity of any one pharmacist is fixed, the output of a pharmacy has become constrained. Consequently, the labor and total cost per prescription continues to rise. The December 2000 Department of Health and Human Services Report to Congress titled "The Pharmacist Workforce: A Study of the Supply and Demand for Pharmacists", which is hereby incorporated by reference into the present application, provides an overview of the above problem.

Due to these increased demands on a pharmacist's time, and the resulting increased reliance on technicians and other non-professional staff to fill prescriptions, there is an increased chance for prescription error. While these errors may take many forms, the likelihood of a dangerous or life threatening "adverse drug event" increases proportionally with the increased chance of prescription fill error. Several studies have shown that prescription error rates are consistently in the 2% to 7% range, with a 4% error rate often cited as a reliable average. The number of deaths due to medication errors is estimated to exceed 7,000 per year in the United States alone. Of course, this number does not include non-fatal conditions from drugs that also result in some form of trauma or injury. The resulting litigation costs associated with these prescription fill errors have also dramatically increased.

Many existing pharmacy filling systems and procedures still require a human operator, whether that operator is a technician or a licensed pharmacist, to validate visually whether the drug that is delivered to the customer is correct. Thus, the human factor can contribute to the majority of prescription fill errors. Existing visual verification techniques typically rely on comparing an electronic image of the prescribed medication, i.e., a picture of the prescribed medication retrieved from a data library, with the actual medication that is dispensed for the patient. Other systems and procedures rely on comparing the dispensed medication with that in the original manufacturer's supply container, or comparing an electronic image of the filled prescription with an electronic image of the prescribed medication retrieved from a data library.

Each of these verification systems present similar problems. First, these known verification methods assume that all drugs are visually distinct. This assumption causes many problems because many drugs are not, in fact, visually distinct and, in other cases, the visual differences between drugs is very subtle. For instance, manufacturers are rapidly running out of unique shapes, colors and sizes for their solid dosage form products. To further complicate the problem, generic drug manufactures may be using shapes, colors, and sizes that are different than that of the original manufacturer. Second, even though some known systems may utilize a National Drug Code (NDC) bar code to verify that the supply bottle being accessed corresponds correctly to the patient's prescription, a fraction of filled prescriptions that are never picked up are returned to the supply shelves for reuse in later prescriptions. These reused bottles will not, therefore, have a manufacturer's bar code on them. It is, therefore, difficult, if not impossible, to incorporate such validation schemes for these unused prescriptions. Furthermore, in these circumstances, a supply bottle is not available for a visual comparison with the filled prescription. Finally, each of these known manual verification and validation techniques typically requires that the pharmacist spend a significant portion of his day performing these administrative or clerical tasks and allows less time for patient consultation and other professional pharmacist activities.

Solid dosage pharmaceuticals (e.g. pills, tablets, and capsules) each have a unique chemical composition associated with them. This is often referred to as a chemical signature or fingerprint. Pharmaceuticals with varying dosage levels of the same active ingredient may have unique chemical signatures as well. Even slight variations in the active ingredient typically produce a unique chemical signature. In that regard, most pharmaceuticals can be identified accurately by the use of some form of chemical analysis. This same methodology may be applied to other forms of medication (e.g. liquids, creams, and powders). Particularly with solid dosage pharmaceutical products, while a group or package of products may look identical in the visible portion of the spectrum each product may have a unique chemical signature in the near-infrared wavelength range (800 to 2500 nm). For example, U.S. Pat. No. 6,771,369 to Rzasa et al. describes a pharmaceutical discrimination system that relies on NIR for scanning the contents of a pharmaceutical vial. As another example, U.S. Pat. No. 7,218,395 to Kaye et al. describes the use of Raman spectroscopy for scanning vial contents. U.S. Patent Publication No. 20080183410 describes another spectroscopy-based discrimination system that can analyze pharmaceuticals as they are present in a capped pharmaceutical vial.

Although these spectroscopy systems can be very accurate, in many instances it may be necessary or helpful to verify the identity of the pharmaceutical visually. Naturally, if the pharmaceutical has already been dispensed into a vial, removal from the vial (or even uncapping of the vial) can slow the dispensing process. However, it is common for pharmaceutical vials to be largely transparent and have an amber color. The use of amber-colored vials began as an attempt to preserve the potency of the pharmaceuticals contained therein (based on the belief that amber coloration helped to prevent the passage of UV radiation, which might damage the pharmaceuticals), and their use has continued as a matter of convention. Thus, the use of a conventional vision system to verify the contents of a vial visually is difficult, because often the color of the pharmaceutical is one of its most distinguishing characteristics, and the amber color of the vial can adversely affect the accuracy of the color presented to the vision system.

In view of the foregoing, it may be desirable to provide a vision system that can accurately detect pharmaceuticals, including their color, while inside a capped pharmaceutical vial.

SUMMARY OF THE INVENTION

As a first aspect, embodiments of the present invention are directed to a method of producing an image of an object residing inside a transparent container of a first color. The method comprises: illuminating the container and the object with light of a second color, the second color being substantially the inverse of the first color; and producing an image of the object through the container. An image produced by this method can exhibit substantially the same color as the object itself, even when the image is taken through a colored transparent wall.

As a second aspect, embodiments of the present invention are directed to a method of producing an image of an object residing inside a transparent container of a first color. The method comprises: illuminating the container and the object with light of a second color, the second color being chosen to substantially cancel the first color; and producing an image of the object in the container. Again, this method can produce an image of the object that is substantially the same color as the object itself.

As a third aspect, embodiments of the present invention are directed to a method of producing an image of an object, comprising: positioning an object such that a transparent colored wall of a first color is between the object and a light source; illuminating the wall and the object with light of a second color, the second color being substantially the inverse of the first color; and producing an image of the object through the wall.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF EMBODIMENTS OF THE INVENTION

Figure 1:
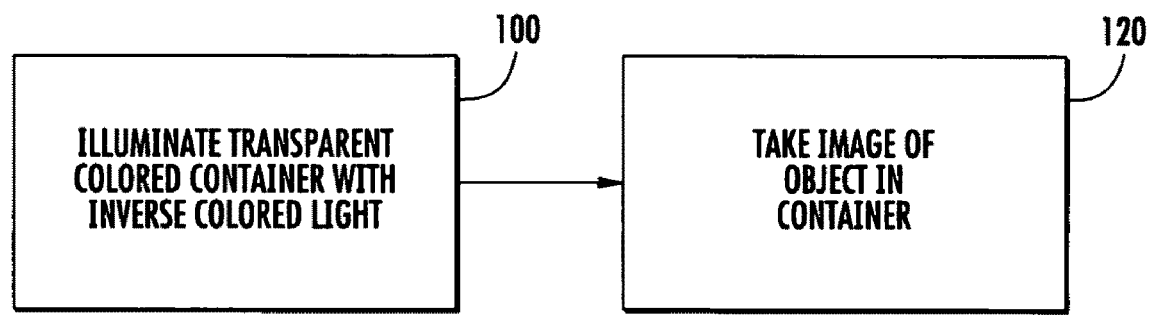
FIG. 1 is a flow chart showing a method of producing an image according to embodiments of the present invention.

The present invention will now be described more fully hereinafter, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout. Thicknesses and dimensions of some components may be exaggerated for clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the expression "and/or" includes any and all combinations of one or more of the associated listed items.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Well-known functions or constructions may not be described in detail for brevity and/or clarity.

Turning now to FIG. 1, a method of producing an image according to embodiments of the present invention is illustrated therein. The method comprises as a first step illuminating a transparent colored container in which an object resides, wherein the container is of a first color, and the illuminating light is of a second color that is substantially the inverse of the first color (box 100). The method further includes the step of producing an image of the object through the container (box 120). These steps are discussed in greater detail below.

As described above, producing an accurate color image of an object within a transparent colored container, such as a pharmaceutical vial, can be problematic. Many pharmaceutical vials are an amber color. Because vision-based inspection/verification systems often rely on color as an identifying characteristic of the object in question, the presence of an amber-colored vial can significantly affect an image of the object taken by the vision system through the wall of the vial; i.e., the amber color of the vial lends an amber tint to the object so that an image taken of the object through the container does not accurately depict the color of the object. Also, if the object is the same color (or similar in color) as the container, the object may be difficult to discern at all. Thus, vision-based inspection/verification systems that rely on the accuracy of the color of the object may be unsuccessful.

In embodiments of the present invention, the inability of conventional vision systems to provide a color-accurate image of the objects in a colored transparent container can be addressed. More specifically, according to embodiments of the present invention, illuminating the container with light of a color that is the "inverse" of the color of the transparent container can enable an imaging device to obtain an image of the object that is accurate in color.

As used herein, the "inverse" of a first color is the color that is "opposite" the first color in a "red/green/blue" (RGB) color scheme. In many color schemes, colors can be represented by percentages or ratios of these three base colors. For example, in one RGB system, the amount of each of red, green and blue in a color is represented as a number from 0 to 255, with 0 representing none of the base color and 255 representing a full amount of the base color. Examples of colors under this scheme are listed in Table 1 below.

TABLE 1

| Red | Green | Blue | Observed Color |
|---|---|---|---|
| 255 | 0 | 0 | Red |
| 0 | 255 | 0 | Green |
| 0 | 0 | 255 | Blue |
| 0 | 0 | 0 | Black |
| 255 | 255 | 255 | White |
| 255 | 255 | 0 | Yellow |
| 255 | 0 | 255 | Pink |
| 0 | 255 | 255 | Light Blue |
| 130 | 130 | 130 | Gray |
| 130 | 0 | 130 | Purple |
| 0 | 130 | 130 | Teal |
| 130 | 130 | 0 | Yellowish-Brown |

Other combinations of red, green and blue yield other colors. The "inverse" of a color would be the color that has the color components that are the "opposite", or the additive inverse, of the color in question according to a particular color scheme. In the 0-255 RGB scheme exemplified above, the "inverse" of an observed color would be the color components that fit the formula (255—R, 255—G, 255—B), wherein "R" is the value of the red component of the observed color, "G" is the value of the green component of the observed color, and "B" is the value of the blue component of the observed color. Using some of the examples from Table 1 above, Table 2 shows the "inverse" colors of the colors listed.

TABLE 2

| Observed Color | Red | Green | Blue | Inverse Red | Inverse Green | Inverse Blue | Inverse Color |
|---|---|---|---|---|---|---|---|
| Red | 255 | 0 | 0 | 0 | 255 | 255 | Light Blue |
| Green | 0 | 255 | 0 | 255 | 0 | 255 | Pink |
| Blue | 0 | 0 | 255 | 255 | 255 | 0 | Yellow |
| Black | 0 | 0 | 0 | 255 | 255 | 255 | White |
| White | 255 | 255 | 255 | 0 | 0 | 0 | Black |
| Yellow | 255 | 255 | 0 | 0 | 0 | 255 | Blue |
| Pink | 255 | 0 | 255 | 0 | 255 | 0 | Green |
| Light Blue | 0 | 255 | 255 | 255 | 0 | 0 | Red |
| Gray | 130 | 130 | 130 | 125 | 125 | 125 | Gray |
| Purple | 130 | 0 | 130 | 125 | 255 | 125 | Mint Green |
| Teal | 0 | 130 | 130 | 255 | 125 | 125 | Salmon |
| Yellowish-Brown | 130 | 130 | 0 | 125 | 125 | 255 | Periwinkle |

As noted above, a typical pharmaceutical vial has an amber color. As an example, a typical vial may have an RGB color value of (200, 120, 10), which is an amber hue. The inverse of this amber color would have an RGB color value of (55, 135, 245), which is a blue hue. Typically, an amber vial will range in color between about (140-235, 70-160, 0-35); thus, the inverse color for the illuminating light range from (20-115, 95-185, 220-255).

Illumination of the container with light of the "inverse" color can be achieved in any number of ways. In some embodiments, the light may be directed on the portion of the container through which the image will be taken. In other embodiments, most or all of the container is bathed in light of the "inverse" color. In some specific embodiments, light is directed to the bottom end of a pharmaceutical vial that contains pharmaceutical tablets.

In certain embodiments of the present invention, the color of the light employed to illuminate the container may be adjusted based on the color of the container. In such a method, the color of the container may be identified with a vision system or the like under known lighting conditions, then converted to digital form. The inverse of the color of the container can then be calculated, and the light used to illuminate the container can be of the calculated inverse color.

Also, in some embodiments, the container is housed in a darkened chamber that obscures ambient light from the container. This type of arrangement can ensure that the color of the light that reaches the vial has the desired RGB values that comprise the inverse color of the container rather than being modified by ambient light.

It has been demonstrated that, by illuminating a transparent amber vial with a blue hue that is substantially the inverse of the amber color of the vial, an image of pharmaceutical tablets residing in the vial taken through the vial has substantially the same color as the tablets themselves. The combination of a colored transparent container with the illumination by light of a substantially inverse color can have the effect of "canceling" the color of the container, such that the image taken through the container is that of the tablets as though the container contained no color.

This similarity of color of the tablets in the vial and the image enables the image of the tablets to be used in an assessment of their color. In some embodiments, the image may be compared to a stored image of the tablet in the container in order to determine the identity of the tablet. In other embodiments, the color of the image may be compared to a stored color chart or table for matching purposes. The image may also be used in a manual verification by a pharmacist to allow him/her to assess the color of the tablet without uncapping the vial.

In some embodiments, the image can be taken with a digital camera. An exemplary camera is Model No. Lw570C, available from Lumenera, Ottawa, Canada. Images can be stored to provide a record of the identity of the pharmaceutical dispensed should the need for such a record ever arise.

In an identification system, color may be used as one identifying characteristic of the tablet or other object in the container. Other attributes that may be assessed and used in conjunction with color to identify the object include size, shape, thickness, topographical features such as score lines or the like, text, numbers or symbols, or other visually-identifying features. Exemplary characteristics for pharmaceutical tablets are discussed in U.S. Pat. No. 6,535,637 to Wootton et al., the disclosure of which is hereby incorporated herein by reference in its entirety.

The method described above may be used in conjunction with other identifying systems and techniques. For example, in a pharmaceutical identification system, the method may be employed in combination with a spectroscopy-based system, such as that described in U.S. patent application Ser. No. 11/972,849, filed Jan. 11, 2008, the disclosure of which is hereby incorporated herein in its entirety. The system described therein employs Raman spectroscopy to identify a pharmaceutical, although other systems that employ electromagnetic radiation outside of the visible light range may also be used. Such combined systems may employ spectroscopy to confirm the identity of the pharmaceutical identified with the present method; conversely, the present method may be employed to confirm the identity of the pharmaceutical identified via spectroscopy.

Those skilled in this art will recognize that the present method may be practiced on objects other than pharmaceuticals and containers other than pharmaceutical vials. For example, the method can be used to scan for eye color even if the subject is wearing tinted glasses or contact lenses. Other investigative or surveillance work, including taking images from inside vehicles with tinted windows/windshields, may also be performed using the present method. In addition, military surveillance may also be carried out with this method. Food and drink inspection, for quality control purposes, may benefit from the present method. Other applications in which the color of an object positioned behind a colored, transparent wall will be apparent to those of skill in this art.

The present invention will now be described in more detail in the following non-limiting example.

EXAMPLE

Figure 2:
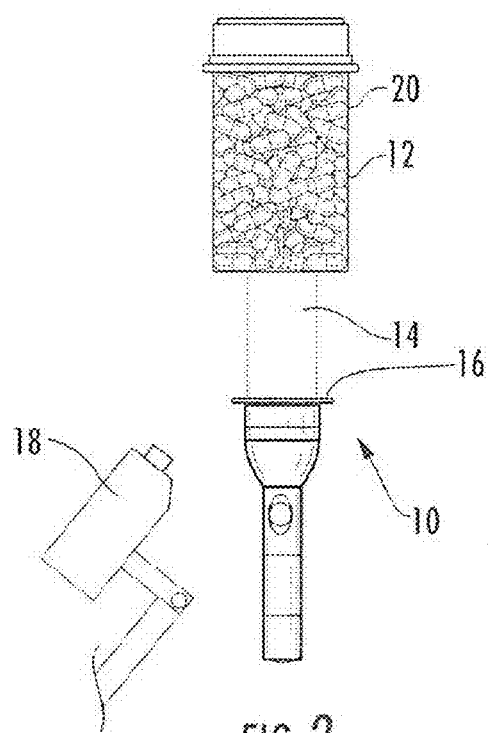
FIG. 2 is a schematic illustration of a system for producing an image of pharmaceutical tablets in a pharmaceutical vial according to embodiments of the present invention.

Referring to FIG. 2, a system 10 that can be used to practice the above-described method is schematically illustrated therein. A colored, transparent container 12 containing a plurality of objects 20 receives light 14 that passes through a colored sheet 16 before reaching the container 12. The sheet 16 is the inverse color of the container 12. A camera 18 takes an image of the objects inside of the container 12.

Figure 3A:
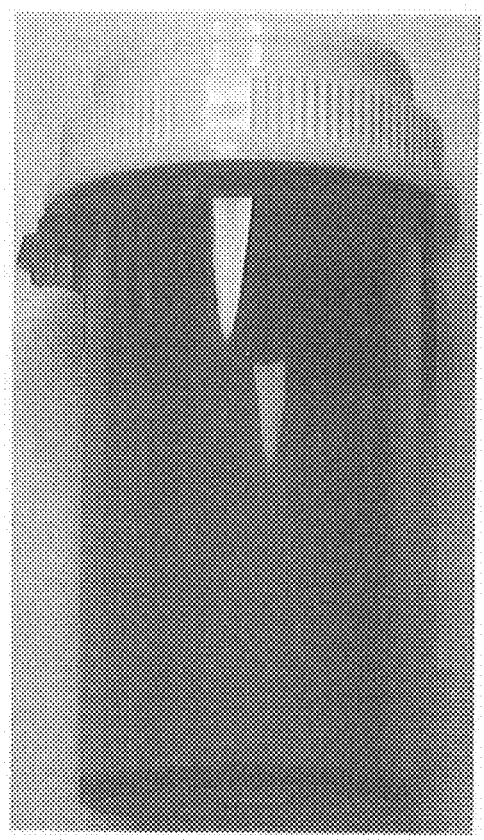
FIG. 3A is a photograph of an exemplary pharmaceutical vial of amber color.
Figure 3B:
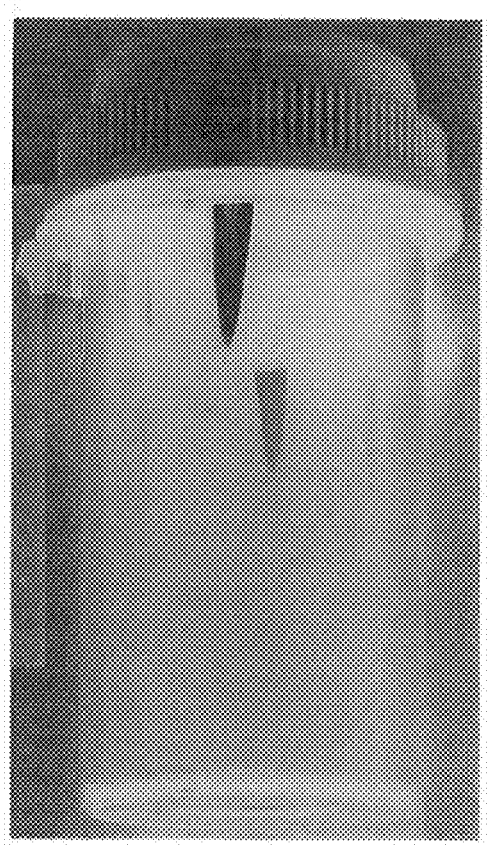
FIG. 3B is an image of the vial of FIG. 3A printed in inverse color.

The color of the light that reaches the camera was selected by first taking a photograph of a pharmaceutical vial (FIG. 3A), using the "inverse" feature in PAINT® graphics software (available from Microsoft, Inc., Seattle, Wash.) to create the RGB inverse of the image of the vial, then printing a copy of the inverse image (FIG. 3B). Light passing through the printed copy took on the reverse color of the image of the vial.

Figure 4A:
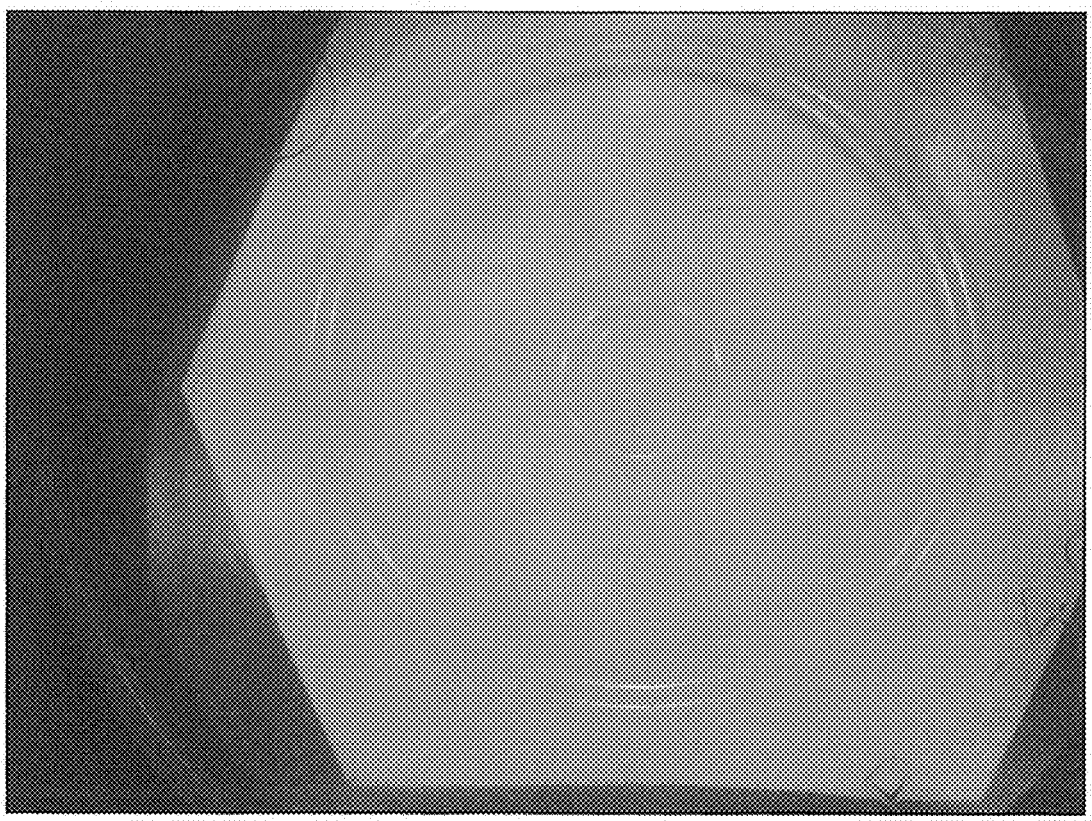
FIGS. 4A and 4B are photographs comparing the image of a test sample in a transparent amber pharmaceutical vial under ordinary light (FIG. 4A) and the image of the test sample under light passing through a transparent material of an "inverse amber" color (FIG. 4B).
Figure 4B:
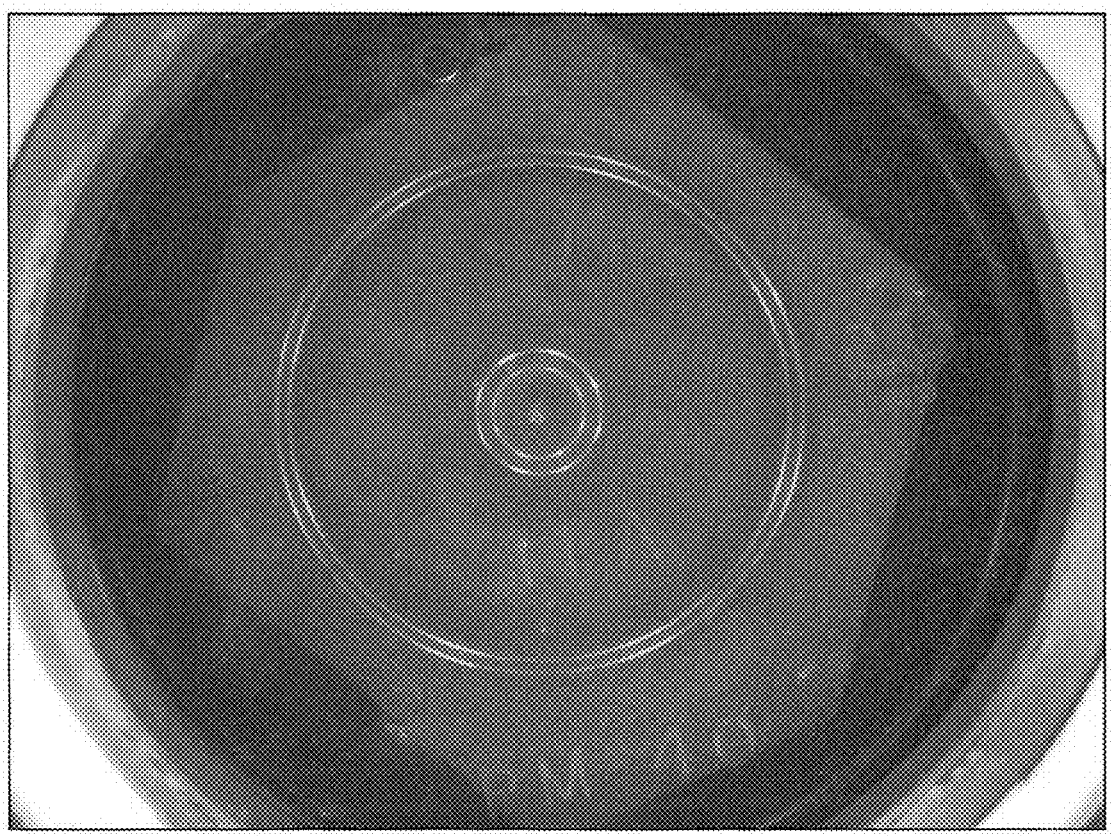

The difference between images obtained with white light and inverse light can be seen in FIGS. 4A and 4B. FIG. 4A shows the image of a test sample taken through the bottom surface of an amber pharmaceutical vial illuminated with white light. As can be seen in FIG. 4A, the handwriting on the test sample (in yellow and orange ink) is largely invisible. FIG. 4B is an image of the same test sample taken through the same vial while the vial was illuminated with light of the inverse color of the amber of the vial (in this instance, a bluish light). As can be seen in FIG. 4B, the handwriting on the test sample, including the orange and yellow ink, was very visible.

The foregoing is illustrative of the present invention and is not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. The invention is defined by the following claims, with equivalents of the claims to be included therein.

That which is claimed is:

1. A method of producing an image of an object residing inside a transparent container of a first color, comprising:
   illuminating the container and the object with light of a second color, the second color being substantially the inverse of the first color;
   producing an image of the object through the container; and
   comparing the image with a stored image of a similar object.

2. The method defined in claim 1, wherein the first color is amber, and the second color is blue.

3. The method defined in claim 1, wherein the first color is defined by the RGB range (140-235, 70-160, 0-35), and the second color is defined by the RGB range (20-115, 95-185, 220-255).

4. The method defined in claim 1, wherein the object is a pharmaceutical.

5. The method defined in claim 4, wherein the object is a pharmaceutical tablet.

6. The method defined in claim 1, wherein the container is a pharmaceutical vial.

7. The method defined in claim 1, further comprising the steps of:
   detecting the first color prior to the illuminating step; and
   selecting the second color responsive to the detecting step.

8. A method of producing an image of an object residing inside a transparent container of a first color, comprising:
   illuminating the container and the object with light of a second color, the second color being chosen to substantially cancel the first color;
   producing an image of the object in the container; and
   comparing the image with a stored image of a similar object.

9. The method defined in claim 8, wherein the first color is amber, and the second color is blue.

10. The method defined in claim 8, wherein the first color is defined by the RGB range (140-235, 70-160, 0-35), and the second color is defined by the RGB range (20-115, 95-185, 220-255).

11. The method defined in claim 8, wherein the object is a pharmaceutical.

12. The method defined in claim 11, wherein the object is a pharmaceutical tablet.

13. The method defined in claim 8, wherein the container is a pharmaceutical vial.

14. The method defined in claim 8, further comprising the steps of:
   detecting the first color prior to the illuminating step; and
   selecting the second color responsive to the detecting step.

15. The method defined in claim 8, further comprising the steps of:
   irradiating the object with electromagnetic radiation outside of the visible light range;
   detecting a property of the electromagnetic radiation after irradiation of the object; and
   producing a spectrum of the composition of the object based on the detecting step.

16. A method of producing an image of an object, comprising:
   positioning an object such that a transparent colored wall of a first color is between the object and a light source;
   illuminating the wall and the object with light of a second color, the second color being substantially the inverse of the first color;
   producing an image of the object through the wall; and
   comparing the image with a stored image of a similar object.

17. A method of producing an image of an object residing inside a transparent container of a first color, comprising:
   illuminating the container and the object with light of a second color, the second color being substantially the inverse of the first color;
   producing an image of the object through the container;
   irradiating the object with electromagnetic radiation outside the visible light range;
   detecting a property of the electromagnetic radiation after irradiation of the object; and producing a spectrum of the composition of the object based on the detecting step.

18. A method of producing an image of an object, comprising:
- positioning an object such that a transparent colored wall of a first color is between the object and a light source;
- illuminating the wall and the object with light of a second color, the second color being substantially the inverse of the first color;
- producing an image of the object through the wall;
- irradiating the object with electromagnetic radiation outside the visible light range;
- detecting a property of the electromagnetic radiation after irradiation of the object; and
- producing a spectrum of the composition of the object based on the detecting step.

* * * * *